(12) United States Patent
Vander Kerken et al.

(10) Patent No.: US 6,305,940 B1
(45) Date of Patent: Oct. 23, 2001

(54) DENTAL PROSTHESIS STABILIZER

(76) Inventors: André Vander Kerken, Streepstraat 147 bus 3, B-2950 Kapellen; Jean-Pierre Van Caesbroeck, Paleisstraat 71A, B-2018 Antwerpen, both of (BE)

( * ) Notice: Subject to any disclaimer, the term of this patent is extended or adjusted under 35 U.S.C. 154(b) by 0 days.

(21) Appl. No.: 09/551,750

(22) Filed: Apr. 18, 2000

(30) Foreign Application Priority Data

Apr. 21, 1999 (BE) .................................................. 9900277

(51) Int. Cl.[7] .................................................. A61C 13/12
(52) U.S. Cl. .................................................. 433/179
(58) Field of Search .................................... 433/19, 179

(56) References Cited

U.S. PATENT DOCUMENTS

| | | | |
|---|---|---|---|
| 5,181 | * | 7/1847 | Stuart ..................... 433/179 |
| 2,224,511 | | 12/1940 | Cleven ..................... 433/179 |
| 4,382,783 | * | 5/1983 | Rosenberg ..................... 433/19 |
| 5,562,445 | | 10/1996 | DeVincenzo et al. ..................... 433/19 |
| 5,980,247 | * | 11/1999 | Cleary ..................... 433/19 |

FOREIGN PATENT DOCUMENTS

| | | |
|---|---|---|
| 1 006 478 | 9/1994 | (BE) . |
| 195 46 960 | 6/1996 | (DE) . |
| 887 914 | 11/1943 | (FR) . |
| 784 540 | 10/1957 | (GB) . |

* cited by examiner

Primary Examiner—John J. Wilson
(74) Attorney, Agent, or Firm—Bacon & Thomas, PLLC

(57) ABSTRACT

Dental prosthesis stabilizer consisting of at least two arms (4–5), connected to one another by means of a hinged joint (6), whereby the hinged joint (6) is equipped with a spring (26), and whereby the arms (4–5) are provided with junctures (13,23) in order to fix these arms to a dental prosthesis, and whereby at least one of the arms (4–5) can be extended.

10 Claims, 3 Drawing Sheets

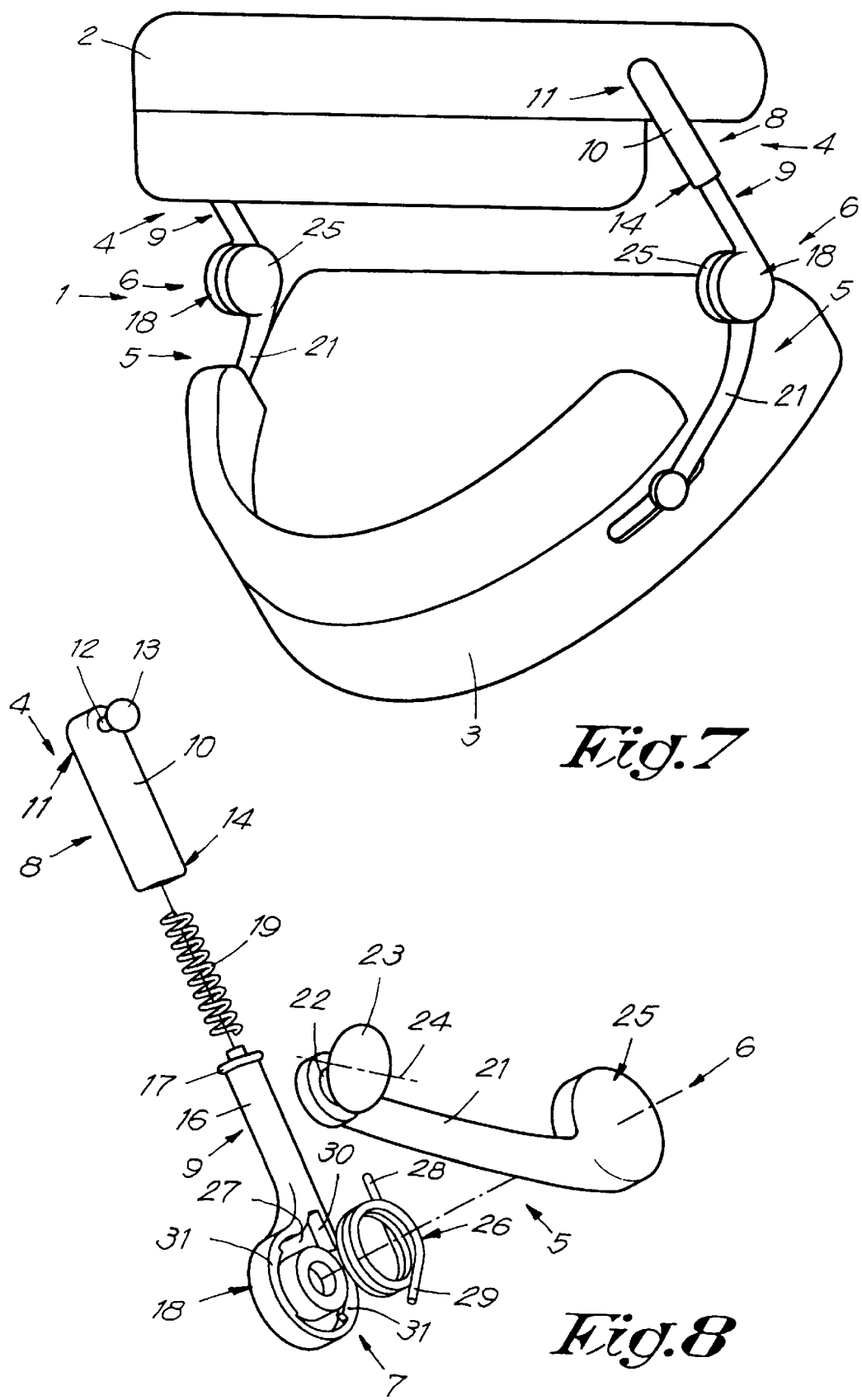

DENTAL PROSTHESIS STABILIZER

BACKGROUND OF THE INVENTION

A) Field of the Invention

The present invention concerns a dental prosthesis stabilizer, in particular a device which makes it possible to stabilize an upper prosthesis and a lower prosthesis in relation to one another.

In particular, the invention concerns a dental prosthesis stabilizer which makes sure that the upper prosthesis remains pressed against the upper jaw, and the lower prosthesis against the lower jaw when the mouth is opened.

B) Discussion of the Related Art

Connections between an upper prosthesis and a lower prosthesis which are equipped with a spring so as to keep the upper prosthesis and the lower prosthesis pressed against the respective jaws when the mouth is opened have already been long known.

Such connections between an upper and a lower prosthesis are described among others in Belgian patent No. 1,006,478 and in British patent No. 784,540.

However, the known connections between either an upper prosthesis and a lower prosthesis, or between an upper prosthesis or a lower prosthesis and the natural teeth have as a major disadvantage that they cannot follow the natural movements of the jaws, as a result of which the prosthesis does not fit up well to the respective jaw when the mouth is opened.

The maxillary joint is indeed situated above and behind the oral cavity, whereas the hinge of a mutual connection between prostheses or between a prosthesis and the natural teeth is necessarily situated in the oral cavity.

As the maxillary joint on the one hand and the above-mentioned connection on the other hand hinge in different places, this has for a result that the prostheses, when the mouth is being opened, make a turning movement having another middle point than that of the respective jaw.

This results in that, when the mouth is opened, the prosthesis will still fit up to the respective jaw in the front of the oral cavity, but this will certainly not be the case in the back of the oral cavity.

SUMMARY OF THE INVENTION

The invention aims a dental prosthesis stabilizer which has been improved in several respects compared to the existing connections of dental prostheses.

In particular, the invention aims a dental prosthesis stabilizer whereby the above-mentioned disadvantage and other disadvantages of the known connections between dental prostheses are excluded or are at least minimized.

To this aim, the invention concerns a dental prosthesis stabilizer, consisting of at least two arms, connected to one another by means of a hinged joint which is equipped with a spring, provided with junctures in order to fix them to a prosthesis, whereby at least one of these arms can be extended.

Preferably, the arm, which is connected to the upper prosthesis, can be extended, to which end said arm is equipped with telescopic parts which slide into one another, in between which is situated a helicoidal compression spring.

According to a preferred embodiment, the arm is provided with a ball, and the upper prosthesis is provided with a cavity, such that the ball forms a snap connection together with the cavity.

The hinged joint between the arms of the dental prosthesis stabilizer may consist of disc-shaped parts of the above-mentioned arms, in between which is situated a torsion spring, and whereby these disc-shaped parts are connected to one another by means of a bayonet catch.

The arm of the dental prosthesis stabilizer which is connected to the lower prosthesis is preferably provided with a knob-shaped protrusion, and the lower prosthesis is preferably provided with a slot in which said knob-shaped protrusion can be provided and can slide into.

BRIEF DESCRIPTION OF THE DRAWINGS

In order to better explain the characteristics of the invention, the following preferred embodiment of a dental prosthesis stabilizer according to the invention is described as an example only without being limitative in any way, with reference to the accompanying drawings, in which:

FIG. 7 represents a view similar to that in FIG. 6, but with the dental prosthesis in open position;

FIG. 8 represents a dental prosthesis stabilizer according to the invention, disassembled and in perspective.

DESCRIPTION OF THE PREFERRED EMBODIMENT

Figure 1:
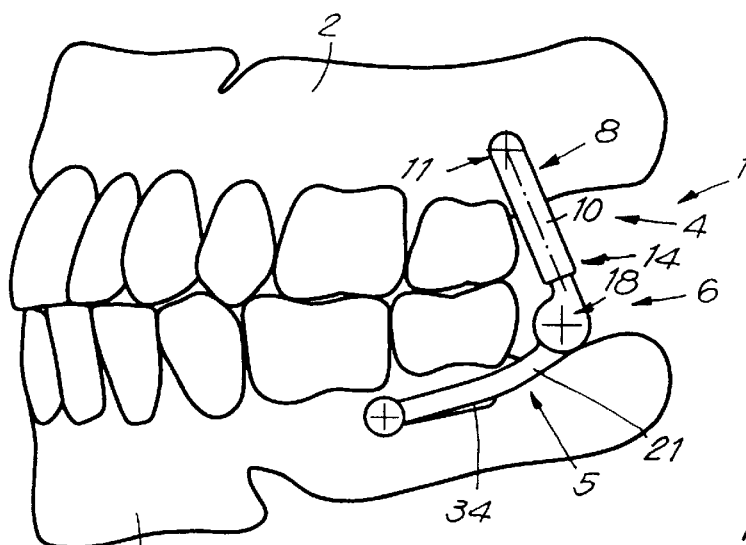
FIG. 1 represents a side view of a dental prosthesis, provided with a dental prosthesis stabilizer according to the invention.
Figure 3:
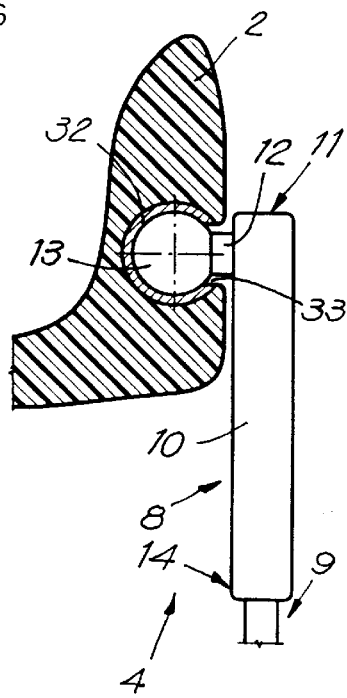
FIG. 3 represents a section according to line III-III in FIG. 2.

The invention concerns a dental prosthesis stabilizer 1 with which an upper prosthesis 2 and a lower prosthesis 3 are attached to one another.

The dental prosthesis stabilizer 1 mainly consists of two arms 4 and 5 which are attached to one another by means of a hinged joint 6.

The two arms 4 and 5 are attached to one another by means of a bayonet catch 7.

The arm 4 consists of two telescopic parts 8 and 9 which slide into one another.

The part 8 of the arm 4 consists of a cylindrical housing 10 which is closed on one end, whereby the housing 10 is provided with a protrusion 12 at the end 11, onto which is fixed a juncture 13 for fixing the arm 14 on the upper prosthesis 2, whereby this juncture in the present embodiment consists of a ball, which further also has 13 as a reference number.

On the other end 14, the cylindrical housing 10 has an inward directed collar 15 on the inner wall.

The part 9 of the arm 4 consists of a small rod 16 which is provided with an outward directed collar 17 on one end, whereas the other end is transformed into a disc-shaped part 18 which is part of the hinged joint 6.

Further, the arm 4 has a helicoidal compression spring 19.

The helicoidal compression spring 19 is shifted in the part 8 of the arm 4 up against the stop 20, after which the above-mentioned collar 17 of the rod 16 is snapped in the part 8 of the arm 4 behind the compression spring 19 by placing the collar 17 behind the collar 15 of the housing 10, which is possible as the housing 10 is made of a somewhat elastic material. Thus, the compression spring 19 is jammed, but nevertheless released, between the stop 20 of part 8 and the end of the rod 16 of part 9.

The arm 5 consists of a bent rod 21, onto which is provided a protrusion 22 on one end onto which is fixed a juncture 23 for fixing said arm 5 on the lower prosthesis 3, whereby said juncture in this embodiment consists of a knob-shaped protrusion in the shape of an oblate ellipsoid, whose short axis 24 is more or less parallel to the bent rod 21, and which further also has 23 as a reference number.

The other end of the rod 21 is transformed into a disc-shaped part 25 which is similar to the disc-shaped part 18 of the arm 4.

The hinged joint 6 consists of the above-mentioned disc-shaped parts 18 and 25 of the respective arms 4 and 5, in between which is situated a torsion spring 26. In the disc-shaped parts 18 and 25 have been made recesses 27 for the torsion spring 26, such that the ends 28 and 29 of the torsion spring 26 in these recesses 27 rest against the stops 30 of the disc-shaped part 18, against the disc-shaped part 25 respectively.

The torsion spring 26 is released when the arms 4 and 5 form an angle of 170 degrees in relation to one another, which more or less coincides with the position of the prosthesis as the mouth is opened wide.

Figure 2:
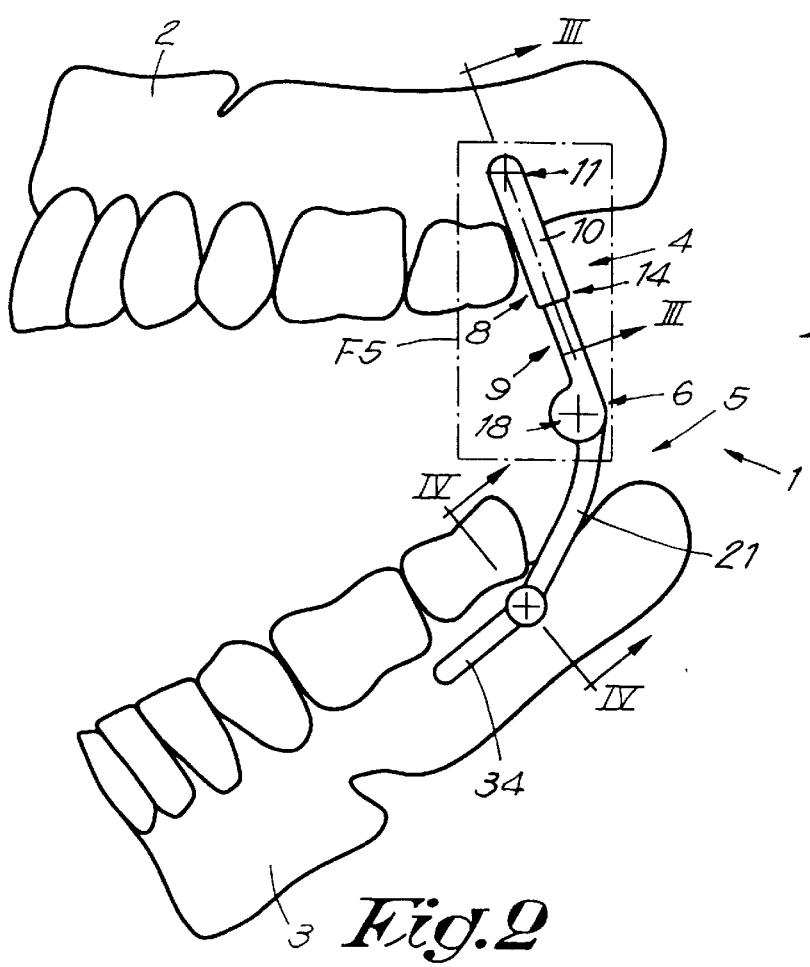
FIG. 2 represents a view, analogous to that in FIG. 1, but with the dental prosthesis in open position.
Figure 4:
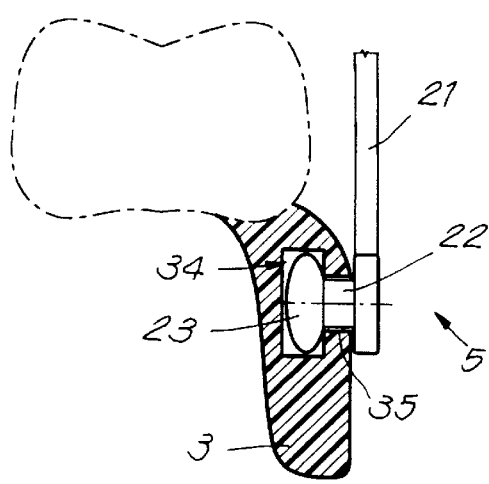
FIG. 4 represents a section according to line IV-IV in FIG. 2.
Figure 5:
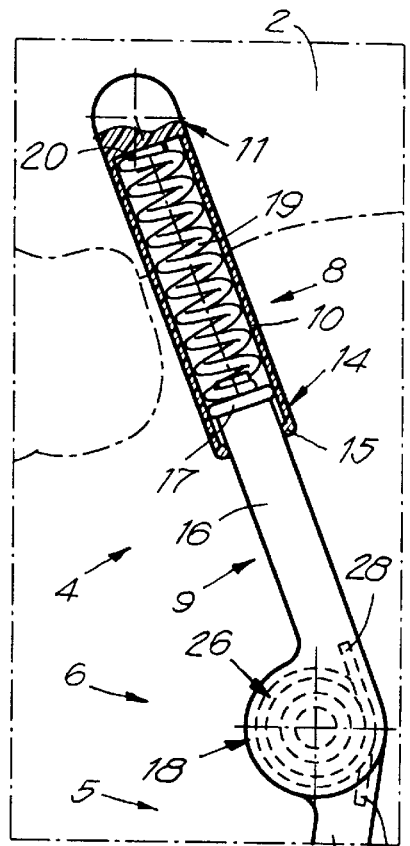
FIG. 5 represents a more detailed view with a partial cut-out of the part which is indicated in FIG. 2 by F5.
Figure 6:
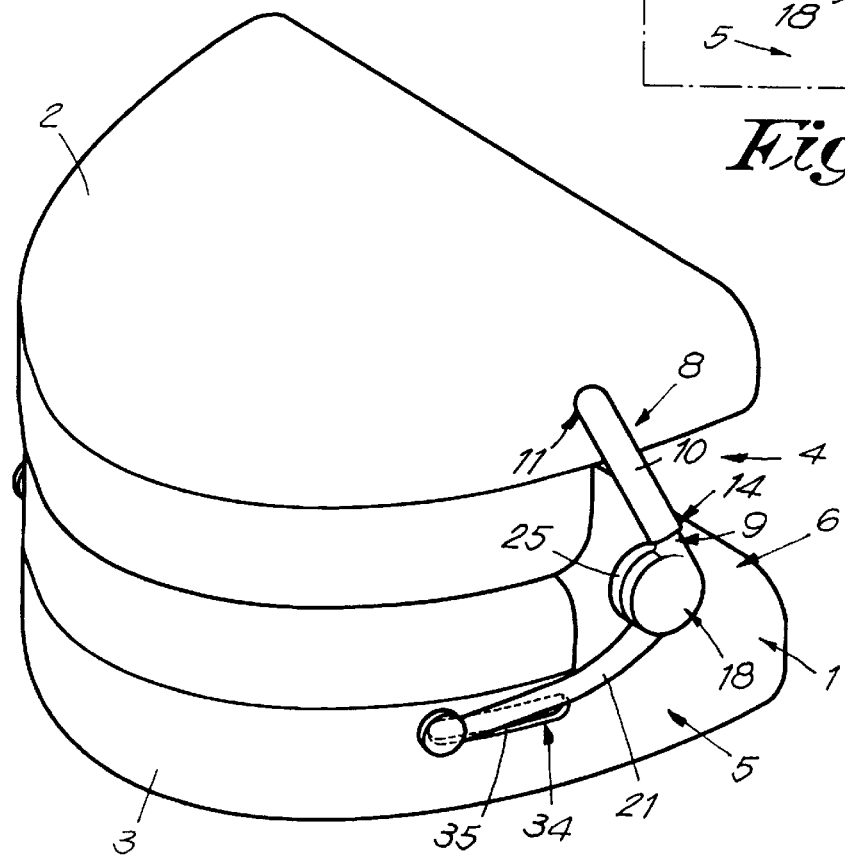
FIG. 6 represents a schematic view in perspective of a dental prosthesis, provided with a dental prosthesis stabilizer according to the invention.

On the side wall of the recesses 27 in the disc-shaped part 18 are provided edges 31, which are designed such that they form a bayonet catch together with edges in the disc-shaped part 25, such that the arms 4 and 5 can be disassembled when they are turned at an angle of 190 to 200 degrees in relation to one another. This is some 20 degrees more than the position represented in FIG. 2, in which the mouth is opened wide.

The dental prosthesis stabilizer 1 is easily attached to the dental prosthesis as follows. In the upper prosthesis 2 is provided a cavity 32 on either side, such that the diameter of the opening 33 of the cavities 32 is a fraction smaller than the diameter of the ball 13 of the arm 4 of the dental prosthesis stabilizer 1. The ball 13 can thus be snapped in the corresponding cavity 32 of the upper prosthesis, loosened from it respectively.

In the lower prosthesis 3 is provided a slot 34 on either side, whereby the width of the opening 35 of said slots 34 is a fraction larger than the short axis 24 of the knob-shaped protrusion 23, but smaller than the long axis of the above-mentioned protrusion 23.

The lower prosthesis 3 is fixed to the dental prosthesis stabilizer 1 by turning it such that the longitudinal direction of the corresponding slot 34 is parallel to the arm 5.

The knob-shaped protrusion 23 of the arm 5 is subsequently pushed in the slot 34, after which the lower prosthesis 3 is tilted back into its normal position.

As the axis 24 of the knob-shaped protrusion 23 is no longer at right angles to the longitudinal direction of the slot 34, the knob-shaped protrusion 23 will at that moment be locked in a slidable manner in the above-mentioned slot 34.

After the assembly, when the compression spring 19 and the torsion spring 25 are released, the prosthesis will be situated in a position which practically coincides with the position of the prosthesis when the mouth is opened wide.

The working of the dental prosthesis stabilizer 1 is very simple and as follows.

When the mouth is opened, the torsion spring 26 on the one hand and the helicoidal compression spring 19 on the other hand are released.

Thanks to this joint release, the lower prosthesis hinges around the hinged joint 6, and the lower prosthesis 3 is simultaneously shifted vertically in relation to the upper prosthesis 2.

In other words, the joint release of the torsion spring 26 and the compression spring 19 makes sure that when the mouth is opened, the lower prosthesis 3 remains pressed against the jawbone.

The forward or backward movement of the lower jawbone is set off by the prosthesis as the dental prosthesis stabilizer 1 is connected to the lower prosthesis 3 in a sliding manner by means of the knob-shaped protrusions 23 which are situated in the slots 34.

It is clear that in this manner is obtained a dental prosthesis stabilizer 1 which provides for an optimal connection of the prosthesis against the jawbones and which moreover guarantees a large freedom of movement for the mouth, so that wearing a dental prosthesis is much more comfortable.

Moreover, the prosthesis can be easily disassembled, whereby the dental prosthesis stabilizer 1 and the dental prosthesis on the one hand, and the arms 4–5 of the dental prosthesis stabilizer 1 on the other hand can be easily disassembled, after which all parts of the dental prosthesis stabilizer 1 can be thoroughly cleaned.

The invention is by no means limited to the above-described embodiments represented in the accompanying drawings; on the contrary, such a dental prosthesis stabilizer can be made in all shapes and dimensions while still remaining within the scope of the invention.

What is claimed is:

1. A dental prosthesis stabilizer to stabilize a linkage between an upper dental prosthesis and a lower dental prosthesis comprising:
    a telescoping first arm having a first end portion and a second end portion, said second end portion forming a protrusion adapted to pivotally connect with a cavity provided by the upper dental prosthesis;
    a second arm having a first end portion and a second end portion, said second end portion forming a protrusion adapted to slidably engage with a slot provided by the lower dental prosthesis; and
    a spring, wherein said first end portion of said first arm is pivotally connected to said first end portion of said second arm to form a hinge joint, said spring being installed on said hinge joint so as to bias the linkage between said first arm and said second arm.

2. The dental prosthesis stabilizer according to claim 1 wherein the first arm includes a cylinder and a rod, said cylinder slidably enclosing one end of said rod.

3. The dental prosthesis stabilizer according to claim 2 wherein a helicoidal compression spring is positioned within said cylinder and communicates with an end of said rod.

4. The dental prosthesis stabilizer according to claim 1 wherein the protrusion of said first arm is generally ball shaped.

5. The dental prosthesis stabilizer according to claim 4 wherein the ball is adapted to snap into said cavity of said upper dental prosthesis.

6. The dental prosthesis stabilizer according to claim 1 wherein said second end portions of said first and second arms each form a disc-shaped portion for housing said spring.

7. The dental prosthesis stabilizer according to claim 6 wherein said spring is a torsion spring.

8. The dental prosthesis stabilizer according to claim 6 wherein said disc-shaped portions are attached to one another by means of a bayonet catch.

9. The dental prosthesis stabilizer according to claim 1 wherein the protrusion of second end portion is generally knob-shaped.

10. The dental prosthesis stabilizer according to claim 9 wherein said knob-shaped protrusion has an enlarged generally ellipsoidal shape, said ellipsoidal shape being dimensioned so as to be slidably retained by the slot of said lower dental prosthesis.

* * * * *